United States Patent [19]

Mittleman

[11] Patent Number: 4,639,019
[45] Date of Patent: Jan. 27, 1987

[54] LUER CONNECTION

[75] Inventor: Herbert Mittleman, Deerfield, Ill.

[73] Assignee: Baxter Travenol Laboratories, Inc., Deerfield, Ill.

[21] Appl. No.: 223,072

[22] Filed: Jan. 6, 1981

Related U.S. Application Data

[63] Continuation of Ser. No. 44,943, Jun. 4, 1979, abandoned.

[51] Int. Cl.⁴ ............................................. F16L 19/02
[52] U.S. Cl. ................................. 285/332; 285/386; 604/283
[58] Field of Search ................. 285/332, 386, 354; 128/214 R, 247, 221; 604/283

[56] References Cited

U.S. PATENT DOCUMENTS

| Re. 29,376 | 8/1977 | Hiszpanski | 285/332 X |
| 2,374,348 | 4/1945 | Harding | 285/332 X |
| 2,511,396 | 6/1950 | Brekke | 285/332 |
| 2,755,801 | 7/1956 | Morando | 128/221 |
| 3,233,925 | 2/1966 | Stevens | 285/354 X |
| 3,411,813 | 11/1968 | Kreuz | 285/332 |
| 3,469,581 | 9/1969 | Burke | 128/221 |
| 3,514,131 | 5/1970 | McKinney | 285/321 X |
| 3,640,551 | 2/1972 | Shakesby | 285/39 |
| 4,076,285 | 2/1978 | Martinez | 285/332 |
| 4,133,312 | 1/1979 | Burd | 285/332 |
| 4,198,076 | 4/1980 | Mezei | 285/18 |

FOREIGN PATENT DOCUMENTS

| 683322 | 12/1966 | Belgium | 285/332 |
| 1204896 | 11/1965 | Fed. Rep. of Germany . |
| 2356093 | 7/1974 | Fed. Rep. of Germany . |
| 2831267 | 2/1979 | Fed. Rep. of Germany . |
| 2127866 | 10/1972 | France . |
| 2395037 | 1/1979 | France . |
| 671480 | 5/1952 | United Kingdom . |
| 1045028 | 10/1966 | United Kingdom | 285/332 |
| 1174948 | 12/1969 | United Kingdom . |
| 1397493 | 6/1975 | United Kingdom . |
| 617654 | 7/1978 | U.S.S.R. | 285/332 |

Primary Examiner—Thomas F. Callaghan
Attorney, Agent, or Firm—Paul C. Flattery; George H. Gerstman; Richard R. Trexler

[57] ABSTRACT

A luer connection device in which a male luer connector includes an outer sleeve that is slideable up a tapered wall so that compression between the outer sleeve and the tapered wall increases as the outer sleeve moves forwardly. An outwardly extending flange is carried by the body of the male luer connector for cooperation with the outer sleeve, to enable the outer sleeve to be unscrewed from a female luer connector without relative rotation of both the main portion of the male luer connector and the outer sleeve.

20 Claims, 3 Drawing Figures

LUER CONNECTION

This is a continuation of application Ser. No. 044,943 filed June 4, 1979 and now abandoned.

BACKGROUND OF THE INVENTION

The present invention concerns an improved luer connection device.

Luer connectors are known in which the male luer connector carries an internally threaded outer sleeve to establish a cooperating threaded engagement with the female luer connector which is externally threaded or carries a radially extending flange. Some prior art luer connection devices have been found to leak and this could result in air embolism or could create contamination problems. Certain prior art luer connection devices have been found difficult to use because once the connection is made, disengagement of the male luer connector from the female luer connector is extremely difficult.

It is an object of the present invention to provide a luer connection device which has a fluid-type connection.

Another object of the present invention is to provide a luer connection device which enables clear inspection of the connection.

A further object of the present invention is to provide a luer connection device in which the mating parts are preloaded prior to locking.

A still further object of the present invention is to provide a luer connection device which is simple in construction and is efficient to manufacture.

Other objects and advantages of the present invention will become apparent as the description proceeds.

SUMMARY OF THE INVENTION

In accordance with the present invention, a luer connection device is provided which includes a male luer connector comprising a tubular body and defining a bore with a front end thereof adapted for insertion into a female luer connector and a rear end thereof adapted for coupling to tubing. The tubular body has a front portion that is contiguous with the front end and a main portion that is separated from the front portion by a sleeve-retaining member. A sleeve is provided having a generally resilient rear portion that is slidable along the main portion. The sleeve also has a front portion that is internally threaded and is adapted for receiving a female luer connector with external threads or an outer flange. The main portion of the tubular body is tapered outwardly in the forward direction. In this manner, increased compression between the rear portion of the sleeve and the main portion of the tubular body occurs as the sleeve is moved forwardly.

In the illustrative embodiment, the sleeve-retaining member comprises an outwardly extending ring carried by the tubular body. The rear portion of the sleeve has a smaller internal diameter than the external diameter of the outwardly extending ring so that the outwardly extending ring prevents forward movement of the rear portion of the sleeve past a predetermined point.

In the illustrative embodiment, the rear portion of the sleeve defines a pair of opposed slots to render the sleeve's rear portion significantly resilient. The tubular body carries a pair of outwardly extending flanges rearward of the main portion, with the flanges and slots being cooperative to prevent relative rotation of the sleeve and tubular body when the flanges are within the slots.

A more detailed explanation of the invention is provided in the following description and claims, and is illustrated in the accompanying drawings.

DETAILED DESCRIPTION OF THE ILLUSTRATIVE EMBODIMENT

Figure 1:
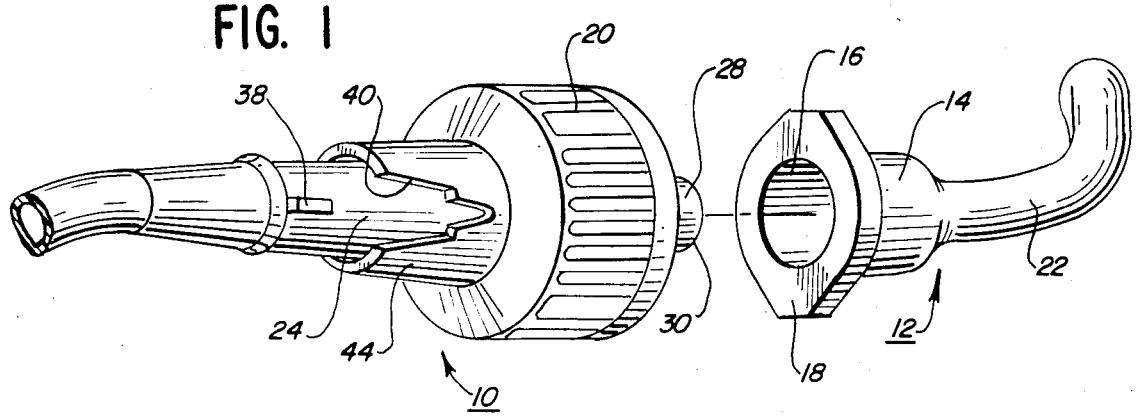
FIG. 1 is a perspective view of a luer connection device constructed in accordance with the principles of the present invention.

Referring to the figures, a luer connection device is shown therein comprising a male luer connector 10 and a female luer connector 12. Female luer connector 12 is of the type in which the main body 14 defines a bore 16 and a flange 18 surrounds bore 16 and extends radially from main body 14. The length of flange 18 is such that it threadedly cooperates with the internal threads of a sleeve 20 carried by male luer connector 10. Plastic tubing 22 is fastened to main body 14 by pressure and solvent sealing as is well-known in the art.

Male luer connector 10 has a tubular body 24 which defines a bore 26 and comprises a front portion 28 contiguous with front end 30 which is adapted for insertion into bore 16 of female luer connector 12. The external surface of front portion 28 is dimensioned so as to provide a snug pressure fit within bore 16.

Tubular body 24 also includes a main portion 32 that is separated from front portion 28 by a sleeve-retaining member 34. In the illustrative embodiment, sleeve-retaining member 34 comprises an outwardly extending ring carried by tubular body 24.

The rear end 36 of tubular body 24 is coupled to plastic tubing with a pressure fit and with solvent bonding. A pair of opposed flanges 38, 39 extend outwardly from tubular body 24 adjacent rear end 36 for cooperation with slots 40 defined by sleeve 20 as discussed below.

Figure 2:
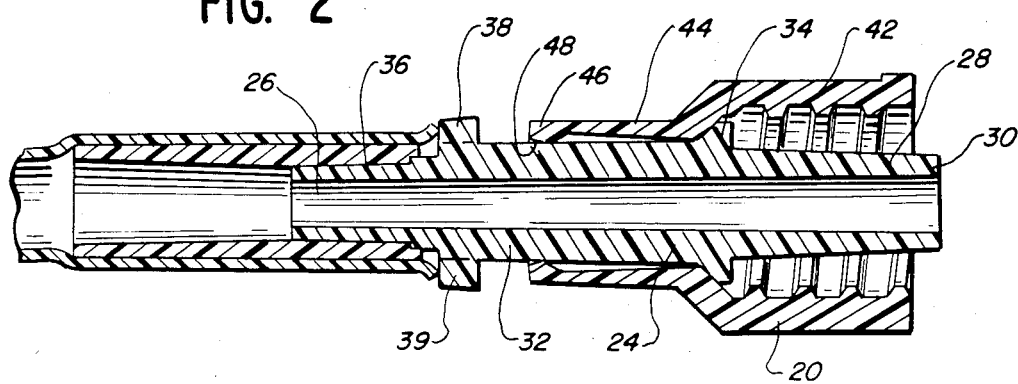
FIG. 2 is a cross-sectional elevation of the male luer connector of the device of FIG. 1.

Sleeve 20 has a front portion 42 that is internally threaded for threaded cooperation with flange 18, and a rear portion 44 that has a small internal diameter than the external diameter of ring 34. Thus, ring 34 serves to prevent sleeve 20 from moving forward past the position illustrated in FIG. 2.

Rear portion 44 has a rear end portion 46 with an inner surface 48 that forms a wiper seal against the surface of main portion 32. Main portion 32 is tapered outwardly in the forward direction so that as sleeve 20 moves forwardly, there will be increased compression between inner surface 48 and the surface of main portion 32. The increased compression ensures that sleeve 20 will not engage flange 18 until front portion 28 is first inserted into bore 16 of female luer connector 12. In certain prior art luer, the coupling of the locking sleeve to the female connector may occur notwithstanding the lack of a secure fluid-tight connection between the male luer and the female luer. Any leakage may cause air embolism. By utilizing an increasing compressive resistance in the present invention, the operator is forced to close the male luer-female luer connection securely before the sleeve 20 can threadedly engage flange 18.

Figure 3:
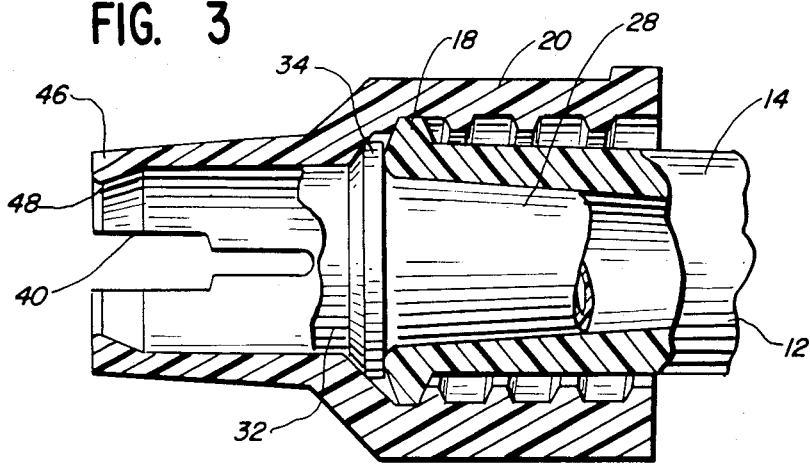
FIG. 3 is an enlarged cross-sectional elevation of the sleeve carried by the male luer connector of FIGS. 1 and 2 and its connection to the female luer connector.

As stated above, rear portion 44 of sleeve 20 defines slots 40 which, as illustrated most clearly in FIGS. 1 and 3, have their widest portion at the rear end 46 of the rear portion 44 and taper inwardly forwardly. These generally V-shaped slots aid in giving the sleeve the proper resilience for movement along main portion 32. In addition, when sleeve 20 is unscrewed from flange 18, flanges 38 and 39 will catch within slots 40 and relative rotation between sleeve 20 and tubular body 24 will be prevented. Prevention of such relative rotation is significant because otherwise it would be extremely difficult to remove male luer connector 10 from female luer connector 12 once the luer connectors are coupled together.

It is desirable that the luer connection device be formed in a plastic molded construction. Sleeve 20 may carry a pair of wings for enabling grasping by the operator for easy insertion and removal of the male luer connector 10 from the female luer connector 12.

It can be seen that inner surface 48 forms a wiper seal or a ring seal which is compressed by the forward movement of sleeve 20 along main body portion 32. The seal formed by inner surface 48 is mated to sleeve 20 so that the sleeve is self-centering.

Although an illustrative embodiment of the invention has been shown and described, it is to be understood that various modifications and substitutions may be made by those skilled in the art without departing from the novel spirit and scope of the invention.

What is claimed is:

1. A luer connection device which comprises:
   a male luer connector comprising a tubular body defining a bore with the front end thereof adapted for insertion into a female luer connector and the rear end thereof adapted for coupling to tubing;
   said tubular body having a front portion contiguous with said front end and a main portion that is separated from said front portion by a sleeve-retaining member;
   a sleeve having a generally resilient rear portion that is slideable along said main portion and having a front portion that is internally threaded and adapted for receiving an outer flange carried by the female luer connector;
   said main portion of said tubular body being tapered outwardly in the forward direction whereby increased compression between the rear portion of the sleeve and said main portion occurs as said sleeve is moved forwardly.

2. A luer connector device as described in claim 1, said sleeve-retaining member comprising an outwardly extending ring carried by said tubular body.

3. A luer connection device as described in claim 1, wherein the rear portion of the sleeve has a smaller internal diameter than the external diameter of said retaining member, whereby said sleeve-retaining member prevents forward movement of the rear portion of the sleeve past a predetermined point.

4. A luer connection device which comprises:
   a male luer connector comprising a tubular body defining a bore with a front end thereof adapted for insertion into a female luer connector and the rear end thereof adapted for coupling to tubing;
   said tubular body having a front portion contiguous with said front end and a main portion that is separated from said front portion by a sleeve-retaining member, said sleeve-retaining member comprising an outwardly extending ring carried by said tubular body;
   a sleeve having a generally resilient rear portion that is slidable along said main portion and having a front portion that is internally threaded and is adapted for receiving an outer flange carried by the female luer connector, the rear portion of the sleeve defining a slot to render the sleeve's rear portion significantly resilient;
   the rear portion of the sleeve having a smaller internal diameter than the external diameter of said retaining member so that the sleeve-retaining member prevents forward movement of the rear portion of the sleeve past a predetermined point;
   said main portion of said tubular body being tapered outwardly in the forward direction whereby increased compression between the rear portion of the sleeve and said main portion occurs as said sleeve is moved forwardly; and
   said tubular body carrying an outwardly extending flange rearward of said main portion, said flange and slot being cooperative to prevent relative rotation of said sleeve and tubular body when said flange is within said slot.

5. A luer connection device which comprises:
   a male luer connector comprising a tubular body defining a bore with a front end thereof adapted for insertion into a female luer connector and the rear end thereof adapted for coupling to tubing;
   said tubular body having a front portion contiguous with said front end and a main portion that is separated from said front portion by a sleeve-retaining member, said sleeve-retaining member comprising an outwardly extending ring carried by said tubular body;
   a sleeve that is slidable along said main portion and having a front portion that is internally threaded and is adapted for receiving an outer flange carried by the female luer connector, the rear portion of the sleeve defining a slot;
   the rear portion of the sleeve having a smaller internal diameter than the external diameter of said retaining member so that the sleeve-retaining member prevents forward movement of the rear portion of the sleeve past a predetermined point; and
   said tubular body carrying an outwardly extending flange rearward of said main portion, said flange and slot being cooperative to prevent relative rotation of said sleeve and tubular body when said flange is within said slot.

6. A luer lock connection device as described in claim 5, said slot having its widest portion at the rear end of said rear portion and tapering inwardly forwardly.

7. A luer connection device which comprises:
   a male luer connector comprising a tubular body defining a bore with the front end thereof adapted for insertion into a female luer connector and the rear end thereof adapted for coupling to tubing;
   said tubular body having a front portion contiguous with said front end and a main portion that is separated from said front portion by a sleeve-retaining member;
   a sleeve having a generally resilient rear portion that is slideable along said main portion and having a front portion that is internally threaded and adapted for receiving an outer flange carried by the female luer connector; the rear portion of the sleeve defining a slot to render the sleeve's rear portion significantly resilient;

said main portion of said tubular body being tapered outwardly in the forward direction whereby increased compression between the rear portion of the sleeve and said main portion occurs as said sleeve is moved forwardly; said tubular body carrying an outwardly extending flange rearward of said main portion, said flange and slot being cooperative to prevent relative rotation of said sleeve and tubular body when flange is within said slot.

8. A connecting device for a fluid transmission set adapted to interconnect with a projecting flange of a first fluid transmission unit having an internal luer tapering chamber comprising:

a mounting member defining a fluid passage means and a longitudinal axis; a length of tubing secured to said member; a collar member rotatably on said member, said collar member having internal threads for engagement with said flange of said first fluid transmission unit; captive means operatively associated with said member to permit free movement along the longitudinal axis thereof while retaining said collar on said member yet permitting rotatable engagement with said flange; a luer tapering extending member for fluid-tight fitment into said internal luer tapering chamber of said first fluid transmission unit; and said captive means including a tapering surface defined by said member for interference with said collar member, said captive means constructed and arranged to permit said collar member to be positioned a substantial distance away from said luer tapering extending member for complete exposure purposes, said captive means further including cooperating means defined by said mounting member and said collar member to provide an interlocking mechanism, said cooperating means positioned on said collar member opposite said internal threads and on said mounting member opposite said tapering surface; so that when said luer tapering extending member is placed in said luer tapering chamber, said collar member will engage said flange and upon rotation of said collar said luer tapering extending member will be forced into fluid-tight engagement and said collar member will contact said tapering surface, and upon a reverse rotation of said collar member and movement of said collar member away from said flange, said interlocking mechanism will interengage whereby rotation of said collar member will cause rotation of said mounting member without rotation of said first fluid transmission unit.

9. The connecting device as defined in claim 8, wherein said interlocking mechanism includes a shoulder member carried by said mounting member.

10. The connecting device as defined in claim 9 wherein said shoulder member is defined by two opposing flanges and said collar member includes two slot portions constructed and arranged to receive said flanges.

11. The connecting device as defined in claim 8 wherein said interlocking mechanism provides a wrench effect between said captive means and said collar member.

12. A connecting device for a fluid transmission set comprising:

a first member defining a fluid passage means and having a longitudinal axis;

a second member defining a fluid passage means and having a longitudinal axis;

tapering interfitment means constructed and arranged with respect to each said member for fluid-tight engagement;

a length of tubing secured to at least one member opposite said tapering interfitment means;

a flange extending from one of said first or second members adjacent said tapering interfitment means;

a collar member longitudinally and rotatably mounted on one of said first or second members opposite said flange, said collar member having internal threads for engagement with said flange; and captive means operatively associated with one of said members and said collar member to permit free movement along the longitudinal axis of said member while retaining said collar on said member yet permitting rotatable engagement with said flange, said captive means including a tapering surface defined by said member mounting said collar for interference therewith, said captive means constructed and arranged to permit said collar member to be positioned a substantial distance away from said tapering interfitment means carried by said member mounting said collar member for complete exposure purposes, said captive means further including cooperating means defined by said member mounting said collar member and said collar member to provide an interlocking mechanism, said cooperating means positioned on said collar member opposite said internal threads and on said mounting member opposite said tapering surface, so that when said tapering interfitment means is interengaged, said collar member will engage said flange and upon rotation of said collar the interfitment means will be forced into fluid-tight engagement and said collar member will engage said tapering surface without rotation of said first or second members, and upon a reverse rotation of said collar member and movement of said collar member away from said flange, said interlocking mechanism will interengage whereby rotation of said collar will cause rotation of said member mounting said collar without rotation of said member with said flange.

13. The connecting device as defined in claim 12 wherein said tapering interfitment means is defined by an internal and external luer fitment with said internal luer fitment and said flange positioned on said first member and said collar and said external luer fitment positioned on said second member.

14. The connecting device as defined in claim 13 wherein said interlocking mechanism includes shoulder members carried by said second member and spaced from said tapering surface of said mounting member.

15. The connecting device as defined in claim 13 wherein said flange is defined by two flanges and extends from said first member positioned immediately adjacent an entrance to said internal luer fitment and interconnected by an annular portion.

16. The connecting device as defined in claim 14 wherein said shoulder members are defined by two oppositely positioned and extending flange members and said collar is defined by two opposing slots constructed and arranged to receive said flange members.

17. The connecting device as defined in claim 16 wherein said flange members extend outwardly from said second member.

18. The connecting device as defined in claim 14 wherein said collar includes an inwardly tapering portion for contact with said tapering surface defined by said mounting member.

19. The connecting device as defined in claim 12 wherein said internal threads of said collar member are continuous.

20. The connecting device as defined in claim 12 wherein said length of tubing is connected to said first member and defines a fluid transmission tubing and said length of tubing is connected to said second member and is fluid transmission plastic tubing.

* * * * *